US010620205B2

(12) United States Patent
Dhanda et al.

(10) Patent No.: US 10,620,205 B2
(45) Date of Patent: Apr. 14, 2020

(54) NMR METHODS FOR ENDOTOXIN ANALYSIS

(71) Applicant: T2 Biosystems, Inc., Lexington, MA (US)

(72) Inventors: Rahul K. Dhanda, Needham, MA (US); Vyacheslav Papkov, Waltham, MA (US); Thomas Jay Lowery, Jr., Belmont, MA (US)

(73) Assignee: T2 Biosystems, Inc., Lexington, MA (US)

( * ) Notice: Subject to any disclaimer, the term of this patent is extended or adjusted under 35 U.S.C. 154(b) by 0 days.

(21) Appl. No.: 14/345,803

(22) PCT Filed: Sep. 20, 2012

(86) PCT No.: PCT/US2012/056312
§ 371 (c)(1),
(2) Date: Mar. 19, 2014

(87) PCT Pub. No.: WO2013/043858
PCT Pub. Date: Mar. 28, 2013

(65) Prior Publication Data
US 2014/0220594 A1    Aug. 7, 2014

Related U.S. Application Data

(60) Provisional application No. 61/576,607, filed on Dec. 16, 2011, provisional application No. 61/537,396, filed on Sep. 21, 2011.

(51) Int. Cl.
*G01N 33/573* (2006.01)
*G01N 24/08* (2006.01)
*G01R 33/50* (2006.01)

(52) U.S. Cl.
CPC ......... *G01N 33/573* (2013.01); *G01N 24/084* (2013.01); *G01R 33/50* (2013.01)

(58) Field of Classification Search
None
See application file for complete search history.

(56) References Cited

U.S. PATENT DOCUMENTS

| | | |
|---|---|---|
| 4,101,435 A | 7/1978 | Hasegawa et al. |
| 4,374,360 A | 2/1983 | Sepponen |
| 4,452,773 A | 6/1984 | Molday |
| 4,875,486 A | 10/1989 | Rapoport et al. |
| 4,920,061 A | 4/1990 | Poynton et al. |
| 5,042,488 A | 8/1991 | Ackerman |
| 5,049,819 A | 9/1991 | Dechene et al. |
| 5,136,095 A | 8/1992 | Tarnowski et al. |
| 5,164,297 A | 11/1992 | Josephson et al. |
| 5,204,457 A | 4/1993 | Maruno et al. |
| 5,254,460 A | 10/1993 | Josephson et al. |
| 5,262,176 A | 11/1993 | Palmacci et al. |
| 5,424,419 A | 6/1995 | Hasegawa et al. |
| 5,445,970 A | 8/1995 | Rohr |
| 5,445,971 A | 8/1995 | Rohr |
| 5,492,814 A | 2/1996 | Weissleder |
| 5,637,469 A | 6/1997 | Wilding et al. |
| 5,801,003 A | 9/1998 | Shimamura et al. |
| 6,013,188 A | 1/2000 | Terstappen et al. |
| 6,165,378 A | 12/2000 | Maruno et al. |
| 6,294,342 B1 | 9/2001 | Rohr et al. |
| 6,297,062 B1 | 10/2001 | Gombinski |
| 6,307,372 B1 | 10/2001 | Sugarman et al. |
| 6,342,396 B1 | 1/2002 | Perrin et al. |
| 6,361,944 B1 | 3/2002 | Mirkin et al. |
| 6,500,343 B2 | 12/2002 | Siddiqi |
| 6,548,311 B1 | 4/2003 | Knoll |
| 6,599,498 B1 | 7/2003 | Groman et al. |
| 6,630,355 B1 | 10/2003 | Pivarnik et al. |
| 6,767,635 B1 | 7/2004 | Bahr et al. |
| 6,866,838 B1 | 3/2005 | Mondain-Monval et al. |
| 6,884,357 B2 | 4/2005 | Siddiqi |
| 6,940,378 B2 | 9/2005 | Miller et al. |
| 7,001,589 B2 | 2/2006 | Mondain-Monval et al. |
| 7,018,849 B2 | 3/2006 | Piasio et al. |
| 7,179,652 B2 | 2/2007 | Cohen et al. |
| 7,217,457 B2 | 5/2007 | Elaissari et al. |
| 7,217,542 B2 | 5/2007 | Tyvoll et al. |
| 7,274,191 B2 | 9/2007 | Park et al. |
| 7,332,353 B2 | 2/2008 | Baudry et al. |
| 7,517,457 B2 | 4/2009 | Siddiqi |
| 7,553,542 B2 | 6/2009 | Ou et al. |

(Continued)

FOREIGN PATENT DOCUMENTS

| | | |
|---|---|---|
| JP | 2000166897 A | 6/2000 |
| JP | 2006162623 A | 6/2006 |
| JP | 3876022 B2 | 1/2007 |
| JP | 3917239 B2 | 5/2007 |
| JP | 2008128883 A | 6/2008 |
| JP | 2008209350 A | 9/2008 |
| WO | WO-1990/006045 A2 | 6/1990 |
| WO | WO-1991/017428 A1 | 11/1991 |
| WO | WO-1997/040181 A1 | 10/1997 |
| WO | WO-1998/004740 A1 | 2/1998 |
| WO | WO-2001/000876 A1 | 1/2001 |

(Continued)

OTHER PUBLICATIONS

Ding et al. Trends in Biotechnology vol. 19, issue 4, pp. 277-281, Aug. 2001.*

(Continued)

*Primary Examiner* — Jana A Hines
*Assistant Examiner* — Khatol S Shahnan Shah
(74) *Attorney, Agent, or Firm* — Clark & Elbing LLP

(57) ABSTRACT

The invention features a method of monitoring a clotting process by measuring a signal characteristic of the NMR relaxation of water in a sample undergoing endotoxi-induced clotting to produce NMR relaxation data and determining from the NMR relaxation data a magnetic resonance parameter of water in the sample characteristic of the level of endotoxin present in the sample.

13 Claims, 6 Drawing Sheets

(56) References Cited

U.S. PATENT DOCUMENTS

| | | |
|---|---|---|
| 7,564,245 B2 | 7/2009 | Lee |
| 7,781,228 B2 | 8/2010 | Menon et al. |
| 7,829,350 B2 | 11/2010 | Josephson et al. |
| 8,339,135 B2 | 12/2012 | Sillerud et al. |
| 8,507,216 B2 * | 8/2013 | Kuroda .................. C12Q 1/66 435/13 |
| 9,157,974 B2 | 10/2015 | Taktak et al. |
| 9,599,627 B2 | 3/2017 | Lowery, Jr. et al. |
| 2002/0102214 A1 | 8/2002 | Briley-Saebo et al. |
| 2003/0054432 A1 | 3/2003 | Chen et al. |
| 2003/0216638 A1 | 11/2003 | Dharmakumar et al. |
| 2003/0219904 A1 | 11/2003 | Cohen et al. |
| 2003/0222648 A1 | 12/2003 | Fan |
| 2004/0175388 A1 | 9/2004 | Ding et al. |
| 2004/0214348 A1 | 10/2004 | Nicholson et al. |
| 2006/0121617 A1 | 6/2006 | Henckel et al. |
| 2006/0269965 A1 | 11/2006 | Josephson et al. |
| 2007/0038121 A1 | 2/2007 | Feldman et al. |
| 2007/0116602 A1 | 5/2007 | Lee |
| 2007/0166730 A1 | 7/2007 | Menon et al. |
| 2008/0199539 A1 | 8/2008 | Baker et al. |
| 2008/0204022 A1 | 8/2008 | Sillerud et al. |
| 2008/0261261 A1 | 10/2008 | Grimes et al. |
| 2008/0305048 A1 | 12/2008 | Josephson et al. |
| 2009/0099342 A1 | 4/2009 | Braconnot et al. |
| 2010/0039109 A1 | 2/2010 | Cheng et al. |
| 2010/0051362 A1 | 3/2010 | Ren et al. |
| 2010/0072994 A1 | 3/2010 | Lee et al. |
| 2010/0120174 A1 | 5/2010 | Josephson et al. |
| 2011/0312002 A1 | 12/2011 | Taktak et al. |
| 2012/0100546 A1 | 4/2012 | Lowery, Jr. et al. |
| 2013/0244238 A1 | 9/2013 | Neely et al. |
| 2013/0260367 A1 | 10/2013 | Lowery, Jr. et al. |
| 2014/0212901 A1 | 7/2014 | Lowery, Jr. et al. |
| 2016/0018421 A1 | 1/2016 | Lowery, Jr. et al. |

FOREIGN PATENT DOCUMENTS

| | | |
|---|---|---|
| WO | WO-2001/011360 A2 | 2/2001 |
| WO | WO-2001/019405 A2 | 3/2001 |
| WO | WO-2002/098364 A2 | 12/2002 |
| WO | WO-2005/099419 A2 | 10/2005 |
| WO | WO-2005/111596 A1 | 11/2005 |
| WO | WO-2008/007270 A2 | 1/2008 |
| WO | WO-2008/010111 A2 | 1/2008 |
| WO | WO-2008/072156 A2 | 6/2008 |
| WO | WO-2008/119054 A1 | 10/2008 |
| WO | WO-2008/137721 A2 | 11/2008 |
| WO | WO-2009/017697 A2 | 2/2009 |
| WO | WO-2009/026251 A1 | 2/2009 |
| WO | WO-2009/045354 A1 | 4/2009 |
| WO | WO-2009/045551 A1 | 4/2009 |
| WO | WO-2009/055587 A1 | 4/2009 |
| WO | WO-2009/061481 A1 | 5/2009 |
| WO | WO-2009/085214 A1 | 7/2009 |
| WO | WO-2010/002479 A1 | 1/2010 |
| WO | WO-2010/051362 A1 | 5/2010 |
| WO | WO-2013/010080 A1 | 1/2013 |
| WO | WO-2013/043858 A1 | 3/2013 |
| WO | WO-2013/190071 A2 | 12/2013 |
| WO | WO-2014/004573 A1 | 1/2014 |

OTHER PUBLICATIONS

Tsuji et al., Applied and Environmental Microbiology vol. 40, No. 3, pp. 533-538, 1980.*

Atanasijevic et al., "Calcium-sensitive MRI contrast agents based on superparamagnetic iron oxide nanoparticles and calmodulin." Proc Natl Acad Sci USA. 103(40):14707-12 (2006).

Author Manuscript of Hong et al., "Magnetic microparticle aggregation for viscosity determination by magnetic resonance." available in PMC Sep. 10, 2009, published in final edited form as, Magn Reson Med. 59(3):515-20 (2008).

Author Manuscript of Koh et al., "Sensitive NMR sensors detect antibodies to influenza." available in PMC Apr. 13, 2009, published in final edited form as Angew Chem. 47(22):4119-21 (2008).

Azoury et al., "Structural changes in fibrin clot associated with the proteolytic activity induced by tissue type plasminogen activator. An NMR study," Biochim Biophys Acta. 295(3):295-300 (1989).

Baudry et al., "Acceleration of the recognition rate between grafted ligands and receptors with magnetic forces." Proc Natl Acad Sci U.S.A. 103(44):16076-8 (2006).

Blackmore et al., "Magnetic resonance imaging of blood and clots in vitro." Invest Radiol. 25(12):1316-24 (1990).

Brooks et al., "Nuclear magnetic relaxation in blood." IEEE Trans Biomed Eng. 22(1):12-18 (1975).

Bryant et al., "Magnetic relaxatiom in blood and blood clots." Magn Reson Med. 13(1):133-44 (1990).

Carr, "Development of platelet contractile force as a research and clinical measure of platelet function." Cell Biochem Biophys. 38(1):55-78 (2003).

Cazenave et al., "Preparation of washed platelet suspensions from human and rodent blood," Methods Mol Biol. 272(1):13-28 (2004).

Chan et al., "Reference values for kaolin-activated thromboelastography in healthy children." Anesth Analg. 105(6):1610-3 (2007).

Clark et al., "Acute hematomas: Effects of deoxygenation, hematocrit, and fibrin-clot formation and retraction on T2 shortening," Radiology. 175(1):201-6 (1990).

Cohen-Tannoudji et al., "Measuring the kinetics of biomolecular recognition with magnetic colloids." Phys Rev Lett. 100(10):108301-1-4 (2008).

Colombo et al., "Femtomolar detection of autoantibodies by magnetic relaxation nanosensors." Anal Biochem. 392(1):96-102 (2009).

Costanzo et al., "Protein-ligand mediated aggregation of nanoparticles: a study of synthesis and assembly mechanism." Chem Mater. 16(9):1775-85 (2004).

Cover, "A robust and reliable method for detecting signals of interest in multiexponential decays," Rev Sci Instrum. 79(5):055106 1-11 (2008).

Craft et al., "A novel modification of the thrombelastograph assay, isolating platelet function, correlates with optical platelet aggregation." J Lab Clin Med. 143(5):301-9 (2004).

De Gaetano et al., "Effect of platelets on clot structuration, a thrombelastographic study." Thromb Res. 3:425-35 (1973).

De Gaetano et al., "Retraction of reptilase-clots in the presence of agents inducing or inhibiting the platelet adhesion-aggregation reaction." Thromb Resear. 2(1):71-84 (1973).

Demas et al., "Portable, low-cost NMR with laser-lathe lithography produced microcoils." J Magn Reson. 189(1):1-20 (2007).

Downey et al., "Novel and diagnostically applicable information from optical waveform analysis of bood coagulation in disseminated intravascular coagulation." Br J Haematol. 98(1):67-73 (1997).

Dreyfus et al., "Microscopic artificial swimmers." Nature. 437(7060):862-5 (2005).

Edzes, "An analysis of the use of pulse multiplets in the single scan determination of spin-lattice relaxation rates." J Magne Reson. 17:301-13 (1975).

Enriquez et al., "Point-of-care coagulation testing and transfusion algorithms." Br J Anaesthe. 103:i14-i22 (2009).

Examination Report for Australian Application No. 2009308841, dated Jun. 24, 2013 (3 pages).

Extended European Search Report for European Patent Application No. 09824124.3, dated Dec. 4, 2013 (13 pages).

Gijs, "Magnetic bead handling on-chip: new opportunities for analytical applications." Microfluid Nanofluid. 1:22-40 (2004).

Gillis et al., "Transverse relaxation of solvent protons induced by magnetized spheres: application to ferritin, erythrocytes, and magnetite." Magn Reson Med. 5(4):323-45 (1987).

Gomori et al., "NMR relaxation times of blood: dependence on field strength, oxidation state, and cell integrity." J Comp Assist Tomog. 11(4):684-90 (1987).

Grimm et al., "Novel nanosensors for rapid analysis of telomerase activity." Cancer Res. 64(2):639-43 (2004).

Hansen et al., "Effect of gel firmness at cutting time, pH, and temperature on rennet coagulation and syneresis: An in situ 1H NMR relaxation study." J Agric Food Chem. 58:513-9 (2010).

(56) References Cited

OTHER PUBLICATIONS

Herbst et al., "A review of water diffusion measurement by NMR in human red blood cells." Am J Physiol. 256:C1097-104 (1989).
Hiltbrand et al., "Variations in proton relaxation in the weak field during coagulation." C. R. Acad Sci. II:1465-7 (1981).
International Preliminary Report on Patentability and Written Opinion for International Patent Application No. PCT/US2012/046669, dated Jan. 23, 2014 (10 pages).
International Preliminary Report on Patentability for International Application No. PCT/US2009/062537, dated Jul. 20, 2011 (16 pages).
International Preliminary Report on Patentability for International Patent Application No. PCT/US2012/056312, dated Mar. 25, 2014 (7 pages).
International Search Report for International Application No. PCT/US2009/062537, dated Dec. 23, 2009 (3 pages).
International Search Report for International Application No. PCT/US2012/046669 dated Oct. 26, 2012 (2 pages).
Istratov et al., "Exponential analysis in physical phenomena." Rev Sci Instrum. 70(2):1233-57 (1999).
Josephson et al., "High-efficiency intracellular magnetic labeling with novel superparamagnetic-Tat peptide conjugates." Bioconjug Chem. 10(2):186-191 (1999).
Josephson et al., "Magnetic nanosensors for the detection of oligonucleotide sequences." Angew Chem. 40(17):3204-6 (2001).
Kim et al., "Magnetic relaxation switch detection of human chorionic gonadotrophin." Bioconjug Chem. 18(6):2024-8 (2007).
Koenig et al., "Theory of $1/T_1$ and $1/T_2$ NMRD profiles of solutions of magnetic nanoparticles." Magn Reson Med. 34(2):227-33 (1995).
Koh et al., "Magnetic nanoparticle sensors." Sensors. 9(10):8130-45 (2009).
Koh et al., "Nanoparticle-target interactions parallel antibody-protein interactions." Anal Chem. 81(9):3618-22 (2009).
Kriz et al., "Advancements toward magneto immunoassays." Biosens Bioelectron. 13(7-8):817-23 (1998).
Kriz et al., "Magnetic permeability measurements in bioanalysis and biosensors." Anal Chem. 68(11):1966-70 (1996).
Kroll, "Thromboelastography: theory and practice in measuring hemostasis." Clin Lab News. 8-10 (2010).
Kötitz et al., "Determination of the binding reaction between avidin and biotin by relaxation measurements of magnetic nanoparticles." J Magn Magn Mater. 194:62-8 (1999).
Landler et al., "In vitro T1- and T2-relaxation times of coagulating blood and thromboses." Z Naturforsch C. 42(9-10):1135-9 (1987) (English Abstract Only).
Lee et al., "Ligand-receptor interactions in chains of colloids: when reactions are limited by rotational diffusion." Langmuir. 24(4):1296-307 (2008).
Lee et al., "Microelectromagnets for the control of magnetic nanoparticles." Appl Phys Letters. 79(20):3308-10 (2001).
Lewin et al., "Tat peptide-derivatized magnetic nanoparticles allow in vivo tracking and recovery of progenitor cells." Nat Biotechnol. 18(4):410-4 (2000).
Liu, "CMOS Magnetic Cell Manipulator and CMOS NMR Biomolecular Sensor," Harvard University Ph.D. dissertation, Nov. 5, 2007 (167 pages).
Lowery, "Nanomaterials-Based Magnetic Relaxation Biosensors," in Kumar, CSSR, Ed. Nanomaterials for the Life Sciences vol. 4: Magnetic Nanomaterials. Weinheim: Wiley-VCH Verlag GmbH & Co. KgaA, (2009) (52 pages).
Makiranta et al., "Master of Science Thesis", Tampere University of Technology, Oct. 2004 (English Abstract Included) (111 pages).
Makiranta et al., "Modeling and simulation of magnetic nanoparticle sensor", Proceedings of the 2005 IEEE, Shanghai, China, Sep. 1-4, 2005, 1256-59 (2005).
Malba et al., "Laser-lathe lithography—a novel method for manufacturing nuclear magnetic resonance microcoils." Biomed Micro. 5(1):21-7 (2003).
Martin et al., "Strong intrinsic mixing in vortex magnetic fields." Phys Rev E Stat Nonlin Soft Matter Phys. 80(1):016312-1-6 (2009).
Martin, "Theory of strong intrinsic mixing of particle suspensions in vortex magnetic fields." Phys Rev E State Nonlin Soft Matter Phys. 79(1):011503-1-12 (2009).
Massin et al., "Planar microcoil-based magnetic resonance imaging of cells", Transducers, Solid-state Sensors, Actuators and Microsystems 12th Int'l conference, Boston, Jun. 8-12, 2003, 967-970.
Massin et al., "Planar microcoil-based microfluidic NMR probes." J Mag Reson. 164(2):242-55 (2003).
Molday et al., "Immunospecific ferromagnetic iron-dextran reagents for the labeling and magnetic separation of cells." J Immuno Meth. 52:353-67 (1982).
Moser et al., "On-chip immune-agglutination assay with analyte capture by dynamic manipulation of superparamagnetic beads." Lab Chip. 9(22):3261-7 (2009).
Niemeyer et al., "Self-assembly of DNA-streptavidin nanostructures and their use as reagents in immuno-PCR." Nucleic Acid Res. 27(23):4553-61 (1999).
Notice of Reasons for Rejection for Japanese Patent Application No. 2011-534756, dated Apr. 2, 2013 (10 pages) (English Language Translation Included).
Notice of Reasons for Rejection for Japanese Patent Application No. 2011-534756, dated Oct. 29, 2013 (10 pages) (English Language Translation Included).
Nummi et al., "Effect of hemolysis and clotting on proton relaxation times of blood." Acta Radiolog Diag. 27(2): 225-30 (1986).
Pell et al., "Optimized clinical T2 relaxometry with a standard CPMG sequence," J Magn Reson Imaging. 23(2):248-52 (2006).
Perez et al., "Magnetic relaxation switches capable of sensing molecular interactions." Nature Biotechnol. 20(8): 816-20 (2002).
Perez et al., "DNA-based magnetic nanoparticle assembly acts as a magnetic relaxation nanoswitch allowing screening of DNA-cleaving agents." J Am Chem Soc. 124(12):2856-7 (2002).
Perez et al., "Use of magnetic nanoparticles as nanosensors to probe for molecular interactions." Chembiochem. 5(3):261-4 (2004).
Perez et al., "Viral-induced self assembly of magnetic nanoparticles allows the detection of viral particles in biological media." J Am Chem Soc. 125(34):10192-3 (2003).
Schuhmacher et al., "NMR relaxation times T1 and T2 of water in plasma from patients with lung carcinoma: correlation of T2 with blood sedimentation rate," Magn Reson Med. 5(6):537-47 (1987).
Sezginer et al., "Very rapid simultaneous measurement of nuclear magnetic resonance spin-lattice relaxation time and spin-spin relaxation time." J Magn Reson. 92:504-27 (1991).
Shapiro et al., "Dynamic imaging with MRI contrast agents: quantitative considerations." Magn Reson Imaging. 24(4):449-62 (2006).
Sillerud et al., "1 H NMR detection of superparamagnetic nanoparticles at 1 T using a microcoil and novel tuning circuit." J Magn Reson. 181(2):181-90 (2006).
Spero et al., "Nanoparticle diffusion measures bulk clot permeability." Biophysical J. 101:1-8 (2011).
Stuhlmuller et al., "Effect of varying fibrinogen and hematocrit concentrations on magnetic resonance relaxation times of thrombus." Invest Radiol. 27(5):341-5 (1992).
Stuhlmuller et al., "Magnetic resonance characterization of blood coagulation in vitro." Invest Radiol. 26(4):343-7 (1991).
Sun et al., "Experimental study on $T_2$ relaxation time or protons in water suspensions of iron-oxide nanoparticles: waiting time dependence." J Magn Magn Mater. 321(18):2971-5 (2009).
Syms et al., "MEMS Helmholtz coils for magnetic resonance imaging." J Micromec Microeng. 15(7):S1-9 (2005).
Tellier et al., "Evolution of water proton nuclear magnetic relaxation during milk coagulation and syneresis: strucural implications." J Agric Food Chem. 41:2259-66 (1993).
Teyssier et al., "Resonance magnetique—dynamique de la coagulation du sang humanin etudiee par dispersion des temps de la relaxation protonique/Coagulation process for human blood studied by protonic relaxation time dispersion," Comptes Rendus de l'Acad. des Sciences. 299(8):395-8 (1984).
Thulborn et al., "Oxygenation dependence of the transverse relaxation time of water protons in whole blood at high field." Biochim Biophys Acta. 714:265-70 (1982).

(56) References Cited

OTHER PUBLICATIONS

Tong et al., "Coating optimization of superparamagnetic iron oxide nanoparticles for high T2 relaxivity." Nano Lett. 10(11):4607-13 (2010).
Tsourkas et al., "Magnetic relaxation switch immunosensors detect enantiomeric impurities." Angew Chem Int Ed Engl. 43(18):2395-9 (2004).
Vidmar et al., "A comparison of the ADC and T2 mapping in an assessment of blood-clot lysability." NMR Biomed. 23(1):34-40 (2009).
Vidmar et al., "Discrimination between red blood cell and platelet components of blood clots by MR microscopy." Eur Biophys J. 37:1235-40 (2008).
Weissleder et al., "Cell-specific targeting of nanoparticles by multivalent attachment of small molecules." Nat Biotechnol. 23(11):1418-23 (2005).
Written Opinion for International Application No. PCT/US2009/062537, dated Dec. 23, 2009, (7 pages).
Wu et al., "1H-NMR spectroscopy on the nanoliter scale for static and on-line measurements." Anal Chem. 66(22):3849-57 (1994).
Notice of Reasons for Rejection for Japanese Patent Application No. 2011-534756, dated Jun. 10, 2014 (3 pages) (English Language Translation Included).
Blinc et al., "Proton NMR study of the state of water in fibrin gels, plasma, and blood clots," Magn Reson Med. 14(1):105-22 (1990).
Extended European Search Report for European Application No. 12812054.0, dated Feb. 23, 2015 (10 pages).
Extended European Search Report for European Patent Application No. 12833431.5, dated May 4, 2015 (5 pages).
Fry et al., "A new approach to template purification for sequencing applications using paramagnetic particles." Biotechniques. 13(1):124-6, 128-31 (1992).
International Search Report and Written Opinion for International Application No. PCT/US2015/027784, dated Jul. 27, 2015 (12 pages).
International Search Report and Written Opinion for International Patent Application No. PCT/US13/73395, dated Mar. 27, 2014 (16 pages).
Li, Yijia, Thesis: "Determining NMR relaxation times for porous media: Theory, measurement and the inverse problem," Master of Mathematics in Applied Mathematics, University of Waterloo, 2007 (147 pages).

Massicotte et al., "Home monitoring of warfarin therapy in children with a whole blood prothrombin time monitor," J Pediatr. 127(3):389-94 (1995).
Office Action for Chinese Application No. 201280044411.X, dated Jan. 6, 2015 (22 pages).
Vidmar et al., "An MRI study of the differences in the rate of thrombolysis between red blood cell-rich and platelet-rich components of venous thrombi ex vivo," J Magn Reson Imaging. 34(5):1184-91 (2011).
"Anti-Clotting Agents Explained," <http://www.strokeassociation.org/STROKEORG/LifeAfterStroke/HealthyLivingAfterStroke/ManagingMedicines/Anti-Clotting-Agents-Explained_UCM_310452_Article.jsp#.Vo6FzmfSmig>, retrieved on Jan. 7, 2016 (2 pages).
Cines et al., "Clot contraction: compression of erythrocytes into tightly packed polyhedra and redistribution of platelets and fibrin," Blood. 123(10):1596-603 (2014).
Examination Report for Australian Application No. 2012281017, dated Jul. 7, 2016 (3 pages).
Extended European Search Report for European Application No. 13860819.5, dated Jun. 30, 2016 (8 pages).
Skewis et al., "T2 magnetic resonance: a diagnostic platform for studying integrated hemostasis in whole blood—proof of concept," Clin Chem. 60(9):1174-82 (2014).
International Preliminary Report on Patentability for International Application No. PCT/US2015/027784, dated Nov. 1, 2016 (7 pages).
Millot, "CPMG pulse program with HADC digitizer and digital filtering for AVANCE AQX spectrometer," <http://web.archive.org/web/20060313160020/http://www.pascal-man.com/pulseprogram/cpmg-HADC-AQX.shtml>, retrieved Mar. 17, 2017 (2 pages).
International Search Report for International Application No. PCT/US09/62537, dated Dec. 23, 2009 (3 pages).
Extended European Search Report for European Application No. 17001484.9, dated Jan. 31, 2018 (8 pages).
International Preliminary Report on Patentability for International Application No. PCT/US2016/039611, dated Dec. 26, 2017 (10 pages).
International Search Report and Written Opinion for International Application No. PCT/US16/39611, dated Sep. 22, 2016 (20 pages).
McIntyre et al., "Reduction in Endotoxin Levels After Performing the Prepare for Aseptic Sort Procedure on the BD FACSAria II Flow Cytometer," BD Biosciences. (2009) (12 pages).

\* cited by examiner

NMR METHODS FOR ENDOTOXIN ANALYSIS

CROSS-REFERENCE TO RELATED APPLICATIONS

This application is the U.S. National Stage filing under 35 U.S.C. § 371 of International Application No. PCT/US2012/056312, filed Sep. 20, 2012, which claims the benefit of the filing date of U.S. Provisional Patent Application No. 61/537,396, filed Sep. 21, 2011, and U.S. Provisional Patent Application No. 61/576,607, filed Dec. 16, 2011.

BACKGROUND OF THE INVENTION

The present invention relates to the field of endotoxin analysis.

Endotoxin is a component of the cell wall in the outer membrane of gram-negative bacteria, and its activity is mainly attributed to LPS (lipopolysaccharide). In the living body, endotoxin exists as a part of the outer membrane in the surface layer of gram negative bacteria. Generally, after death of gram-negative bacteria, endotoxin is liberated and is present in a free form in blood.

When more than a certain level of endotoxin is present in blood, the endotoxin stimulates monocytes, granulocytes, etc., resulting in excessive production of inflammatory cytokines. Consequently, so called endotoxinemia accompanied by symptoms such as fever, sepsis, septic shock, multiple organ failure, etc. is induced. For this reason, detection of endotoxin in pharmaceuticals for injection, etc. is crucial, and thus the bacterial endotoxin test is prescribed by the Japanese, U.S., and European pharmacopeias. From the aspect of clinical diagnosis, precise measurement of blood endotoxin level is considered crucial for early diagnosis and therapeutic effect evaluation.

Examples of a conventional method for measuring endotoxin include the pyrogen test, in which a rabbit is treated with a direct injection of a test sample and measured for increase in body temperature that can be converted into the endotoxin level, and the *Limulus* test utilizing gelation of horseshoe crab amebocyte lysate triggered by endotoxin. The method involving direct injection into a rabbit has problems in cost, length of time required to obtain the test results, and sensitivity, and for this reason, the *Limulus* test currently prevails as a method for measuring endotoxin.

A gelation of horseshoe crab amebocyte lysate is triggered by endotoxin. The gelation process of horseshoe crab amebocyte lysate contains a Factor-C pathway specifically associated with endotoxin. The Factor-C pathway is constituted by the following cascades. First, endotoxin firmly binds with Factor-C, and thereby activates the Factor-C. Then, Factor-C activated by binding with endotoxin (active Factor-C) activates Factor B. Subsequently, activated Factor B (active Factor B) activates a proclotting enzyme, resulting in production of a clotting enzyme. This clotting enzyme partially hydrolyzes its substrate, i.e., coagulogen. As a result, peptide C is liberated from the coagulogen, and a clotting protein, coagulin, is produced. By a coagulation action of the coagulin, gelation occurs.

The *Limulus* test for measuring endotoxin utilizes the above-mentioned gelation process of horseshoe crab amebocyte lysate triggered by endotoxin. As the *Limulus* test, a gel-clot technique, a colorimetric technique using synthetic chromogenic substrates, and a kinetic turbidimetric techniques are established techniques used to evaluate gelation (i.e., clotting, see FIG. 1).

New methods of detection are needed that can (i) increase the limit of detection of endotoxin, (ii) reduce the about of amebocyte lysate required for performing the assay, and/or (iii) allow for the monitoring of samples containing light scattering compositions.

SUMMARY OF THE INVENTION

The invention features a method of measuring the endotoxin level in a sample including the steps of: (a) mixing the sample with LAL reagent to form a mixture; (b) at a predetermined time following step (a), measuring the NMR relaxation rate of water in the mixture; and (c) on the basis of the NMR relaxation rate, determining the endotoxin level in the sample. In particular embodiments, step (b) is repeated (e.g., over the course of 5, 10, 15, 20, 25, or 30 minutes) and the change in the NMR relaxation rate is observed at two or more time points following step (a). The method can further include calculating the change in the NMR relaxation rate (e.g., the change observed between two or more measurements, such as the change in the NMR relaxation rate when compared to prior to, or in the first observation after, the completion of step (a), or a change relative to a threshold NMR relaxation rate value), and, on the basis of the change determining the endotoxin level in the sample.

In one particular embodiment, the endotoxin level is determined within 20 minutes of performing step (a) (e.g., within 5±2, 8±2, 10±5, 15±5, 20±5, 30±5, or 40±5 minutes).

In a related aspect, the invention features a method for identifying the presence of endotoxin in a mixture including LAL reagent, the method including measuring a signal characteristic of the NMR relaxation rate of water in the mixture to produce NMR relaxation data, and on the basis of the NMR relaxation data determining whether the endotoxin is present in the mixture.

In a related aspect, the invention features a method of identifying the presence of endotoxin in a sample by (i) mixing the sample with LAL reagent to form a mixture containing water and Factor-C capable of being activated by binding with endotoxin; (ii) following step (i), making a series of relaxation rate measurements of the water in the mixture capable of undergoing a clotting process to provide two or more decay curves, each decay curve characteristic of a time point in the process; (iii) applying a mathematical transform to the two or more decay curves to produce two or more magnetic resonance relaxation rates, each relaxation rate characteristic of a time point in the process; and (iv) based upon the two or more relaxation rates, determining whether endotoxin is present in the sample.

The invention features a method of identifying the presence of endotoxin in a sample by: (i) mixing the sample with LAL reagent to form a mixture containing water and Factor-C capable of being activated by binding with endotoxin; (ii) following step (i), making at least one relaxation rate measurement of the water in the mixture capable of undergoing a clotting process to provide one or more decay curves, each decay curve characteristic of a time point in the process; (iii) applying a mathematical transform to at least one decay curve to produce at least one magnetic resonance relaxation rate characteristic of a time point in the process; and (iv) based the relaxation rate, determining whether endotoxin is present in the sample. In certain embodiments, step (iv) includes comparing the relaxation rate to a predetermined threshold value.

The invention further features a method of measuring the endotoxin level in a sample by: (i) mixing the sample with LAL reagent to form a mixture containing water and Factor-C capable of being activated by binding with endotoxin; (ii) following step (i), making at least one relaxation rate measurement of the water in the mixture capable of undergoing a clotting process to provide one or more decay curves, each decay curve characteristic of a time point in the process; (iii) applying a mathematical transform to at least one decay curve to produce at least one magnetic resonance relaxation rate characteristic of a time point in the process; and (iv) based the relaxation rate, determining the level of endotoxin present in the sample. In particular embodiments, step (iv) includes comparing the relaxation rate to a predetermined threshold value (e.g., values from a predetermined dose-response curve for endotoxin).

In any of the above methods, the method can be capable of detecting 0.001 EU/mL, 0.0005 EU/mL, or 0.0001 EU/mL in the mixture.

In any of the above methods, the mixture can include from 10% to 50% of the amount of LAL reagent typically used in a turbidometric assay (e.g., 10±5%, 15±5%, 20±5%, 25±5%, 30±5%, or 40±10% of the amount typically used in a turbidometric assay).

In any of the above methods, the sample can include a light scattering or light absorbing composition (e.g., the sample can be unsuitable for a turbidometric assay, but suitable for the methods described herein).

In any of the above methods, the NMR relaxation rate is selected from the group consisting of T1, T2, T1/T2 hybrid, $T_{1rho}$, $T_{2rho}$, and $T_2^*$.

In a related aspect, the invention features a method of measuring the endotoxin level in a sample including: (a) mixing the sample with LAL reagent to form a mixture containing Factor-C capable of being activated by binding with endotoxin; (b) following step (a), measuring a signal characteristic of the NMR relaxation rate of water in the mixture to produce NMR relaxation data; (c) determining from the NMR relaxation data a magnetic resonance parameter value or set of values, the value or set of values being responsive to Factor-C activation by the endotoxin in the mixture; and (d) on the basis of the result of step (c), determining the endotoxin level in the sample. In particular embodiments, the mixture includes one or more populations of water and determining from the NMR relaxation data a magnetic resonance parameter value or set of values correlated to at least one population of water in the sample. In some embodiments, the mixture includes at least three populations of water.

The method can include fitting the measurements to an algorithm that distinguishes two or more separate water populations within the mixture, where each separate water population is characterized by one or more magnetic resonance parameters having one or more values.

The algorithm can be, without limitation, selected from a multi-exponential algorithm, a bi-exponential algorithm, a tri-exponential algorithm, a decaying exponential algorithm, a Laplace transform, a goodness-of-fit algorithm, an SSE algorithm, a least-squares algorithm, a non-negative least-squares algorithm, and any other algorithm described herein. In particular embodiments, the algorithm is an inverse Laplace transform or the algorithm is given by equations (1) or (2).

$$I = Amp_A \exp^{(-t/T2A)} + Amp_B \exp^{(-t/T2B)} + O \quad (1)$$

$$I = Amp_A \exp^{(-t/T2A)} + Amp_A \exp^{(-t/T2B)} + Amp_C \exp^{(-t/T2C)} + O \quad (2)$$

In equations (1) and (2), I is the intensity of a measured value T2; t is time; $Amp_A$ is an extracted coefficient that indicates the degree to which the exponential term $\exp^{(-t/T2A)}$ contributes to a measured T2 intensity; $Amp_B$ is an extracted coefficient that indicates the degree to which the exponential term $\exp^{(-t/T2B)}$ contributes to a measured T2 intensity; $Amp_C$ is an extracted coefficient that indicates the degree to which the exponential term $\exp^{(-t/T2C)}$ contributes to a measured T2 intensity; T2A is an extracted relaxation time that indicates the contribution of a water population A to a measured T2 intensity; T2B is an extracted relaxation time that indicates the contribution of a water population B to a measured T2 intensity; T2C is an extracted relaxation time that indicates the contribution of a water population C to a measured T2 intensity; and O is an offset constant. In any of the above methods, the relaxation rate measurements can include a T2 measurement. The magnetic resonance parameter values can include a T2 parameter value and/or an amplitude parameter value.

In any of the above methods, the signal arises from monitoring protons in water or monitoring oxygen atoms in water.

In any of the above methods, the NMR relaxation data is selected from T1, T2, T1/T2 hybrid, $T_{1rho}$, $T_{2rho}$, and $T_2^*$ data.

The invention features a method of measuring the endotoxin level in a sample including, the method including the steps of: (i) mixing the sample with LAL reagent to form a mixture containing Factor-C capable of being activated by binding with endotoxin; (ii) following step (i), measuring a series of signals characteristic of the NMR relaxation rate of water in the mixture to produce NMR relaxation data; and (iii) determining from the NMR relaxation data a time curve that is characteristic of Factor-C activation by the endotoxin in the mixture. In some embodiment, the time curve is a T1 time curve, a T2 time curve, or a hybrid T1/T2 time curve.

In another aspect, the invention features a method of comparing an endotoxin-induced clotting behavior of a sample measured using the NMR-based techniques of the invention with rheological change or clotting measured in an equivalent sample using a system known in the art.

As used herein, the term "3D data set" refers to a collection of measured and/or derived data points that can be assembled into a 3D plot that is characteristic of the changes in a sample undergoing a clotting process or dissolution process over a period of time. A 3D plot derived from a 3D data set can depict the emergence and/or disappearance of different water populations within the sample and quantifies the intensities and relaxation times (e.g., T2 relaxation times) of these water populations at specific points in time or over ranges of time.

As used herein, the term "a first water population" refers to a water population of an aqueous sample that is characterized by an initial amplitude when unclotted that changes with clotting. A first water population may also refer to a water population referred to elsewhere in the application as population A. The amplitude and T2 data extracted from a first water population are referred to as $Amp_A$ and T2A, respectively.

As used herein, the term "a second water population" refers to a water population of an aqueous sample that is characterized by an initial amplitude when unclotted that changes with clotting. The second water population having a characteristic relaxation time that is different from the first water population. The second water population may be referred to elsewhere in the application as population B. The amplitude and T2 data extracted from a second water population are referred to as $Amp_B$ and T2B, respectively.

As used herein, the term "a third water population" refers to a water population of an aqueous sample that is characterized by a relaxation time that is different from the first water population and the second water population. The third water population may be referred to elsewhere in the application as population C. The amplitude and T2 data extracted from a third water population are referred to as $Amp_s$ and T2C, respectively.

As used herein, the term "algorithm" refers to a mathematical routine used to process or transform data.

As used herein, the term "assay" refers to a method of monitoring endotoxin-induced clotting behavior.

As used herein, the term "clotting behavior" refers to a parameter associated with an endotoxin-induced clot, a forming endotoxin-induced clot, or an endotoxin-induced clot undergoing dissolution (e.g., clotting time, clot strength, kinetic behavior of the clot, clot strength, etc.).

As used herein, the term "clotting process" refers to a process in a liquid resulting in localized spatial change of the solvent water molecules within a sample and characterized by changes in the NMR relaxation rate of solvent water molecules within the aqueous liquid. The aqueous liquid may have more than one population of solvent water molecules, each population characterized by an NMR relaxation parameter that varies as the aqueous sample undergoes the clotting process. Alternatively, the aqueous liquid is in an NMR exchange regime that gives rise to a single population of solvent water molecules for which there is an observable relaxation rate shift during the clotting process. The methods of the invention can be used to monitor an endotoxin-induced clotting process.

As used herein, the term "LAL reagent" refers to both to amebocyte lysates obtained from horseshoe crabs (e.g., *Limulus polyphemus, Carcinoscorpius rotundicauda, Tachypleudus tridentata*, or *Tachypleudus gigas*) and to synthetic LAL reagents. Synthetic LAL reagents include, for example, can include purified horseshoe crab Factor-C protein (naturally occurring or recombinant) and, optionally, a surfactant, as described in WO 03/002976. One such reagent, "PyroGene™," is available from Cambrex Bio Science Walkersville, Inc. Reagents, such as those discussed in U.S. Patent Publication No. 20030054432, can also be used. LAL reagents preferably can be obtained from Cambrex Bio Science Walkersville, Inc. Lyophilized LAL reagent can be reconstituted with 1.4 mL of LAL reagent water (endotoxin-free water) and kept refrigerated until use. A reagent kit that enables highly sensitive measurement of endotoxin using a recombinant Factor-C (trade name: PyroGene rFc, manufacturer: Lonza Walkersville, Inc., distributor: Daiichi Pure Chemicals Co., Ltd.) is commercially available.

As used herein, the term "magnetic resonance parameter" refers to a relaxation rate or amplitude extracted from an NMR relaxation rate measurement.

As used herein, the term "NMR relaxation rate" refers to any of the following in a sample: T1, T2, $T_{1rho}$, $T_{2rho}$, and $T_2^*$. NMR relaxation rates may be measured and/or represented using T1/T2 hybrid detection methods.

As used herein, the term "predetermined threshold value" refers to a standard parameter value or set of values, a standard time curve, or a standard signature curve that is derived from the methods of the invention and is characteristic of a particular rheological state or endotoxin level. A predetermined threshold value can be obtained by measuring the NMR parameter values in, for example, samples with and without endotoxin. Alternatively, the predetermined threshold value can be a predetermined value characteristic of the absence of clotting (i.e., such as in an endotoxin free standard). The predetermined threshold value can be used to ascertain the amount of endotoxin in a sample at a particular time following the mixture of the endotoxin with an LAL reagent. For example, the threshold value can be a water relaxation rate.

As used herein, the term "reader" or "T2reader" refers to a device for detecting coagulation-related activation including clotting of samples. T2readers may be used generally to monitor endotoxin-induced clotting in a sample. Such a device is described, for example, in International Publication No. WO 2010/051362, which is herein incorporated by reference.

As used herein, the term "relative concentration" refers to the comparative concentration of one water population with respect to another (e.g., a second or third) water population. For example, the relative concentration of water population A may be two times (or five times, or ten times) greater than the concentration of water population B.

As used herein, the term "T1/T2 hybrid" refers to any detection method that combines a T1 and a T2 measurement. For example, the value of a T1/T2 hybrid can be a composite signal obtained through the combination of, ratio, or difference between two or more different T1 and T2 measurements. The T1/T2 hybrid can be obtained, for example, by using a pulse sequence in which T1 and T2 are alternatively measured or acquired in an interleaved fashion. Additionally, the T1/T2 hybrid signal can be acquired with a pulse sequence that measures a relaxation rate that is comprised of both T1 and T2 relaxation rates or mechanisms.

As used herein, the term "T2 signature" refers to a curve established by applying a mathematical transform (e.g., a Laplace transform or inverse Laplace transform) to a decay curve associated with a relaxation rate parameter at a discrete time point or over a set time duration during a rheological event. T2 signature curves provide information about the relative abundance of multiple water populations in a clot. T2 signatures may be used advantageously to assess, in real time, a discriminated endotoxin contamination or level in a sample. Further, a T2 signature may be a two dimensional (intensity versus T2 value or T2 value versus time) or three dimensional representation (intensity versus T2 value versus time). The T2 values in the two- or three dimensional representation may be replaced with or compared to other NMR signals such as T1, T1/T2 hybrid, $T_{1rho}$, $T_{2rho}$ and $T_2^*$.

Other features and advantages of the invention will be apparent from the following Detailed Description, the drawings, and the claims.

BRIEF DESCRIPTION OF THE DRAWINGS

FIG. 4A depicts the correlation for a 2% change in T2. FIG. 4B depicts the correlation for a 0.2% change in T2. The strong correlation observed for small changes in T2 permit rapid detection of endotoxin in a sample.

DETAILED DESCRIPTION

Figure 1:
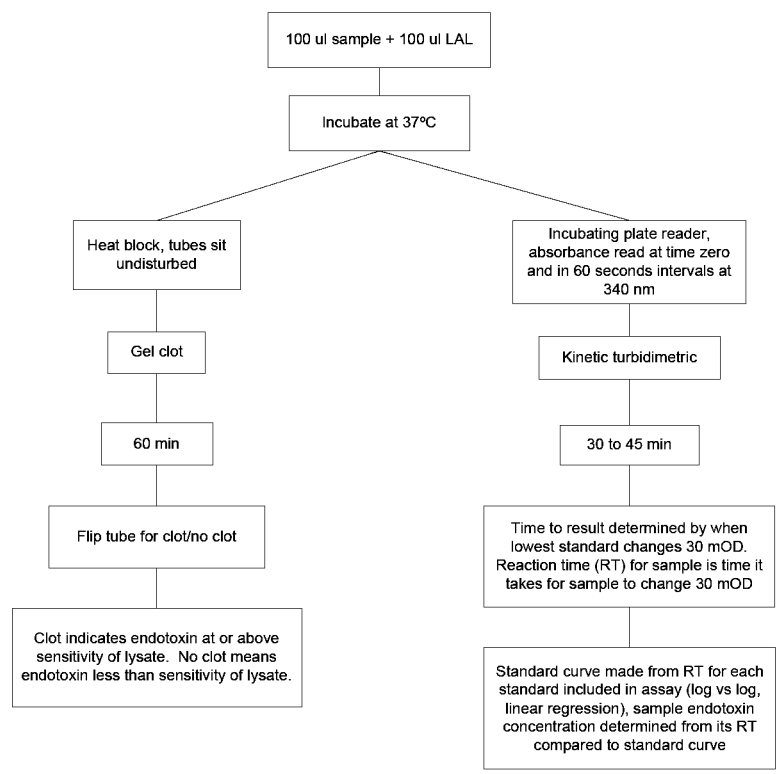
FIG. 1 is a chart depicting LAL procedures for monitoring and measuring endoxtoxin in a sample. The sample can be a negative control (water blank), an endotoxin standard (e.g., for producing a standard curve), a test sample (for determining whether, or how much, endotoxin is present in the sample, and/or a test sample spiked with endotoxin. For such assays, lyophilized LAL is typically reconstituted with LAL Reagent Water (endotoxin-screened water). The endotoxin standard can be available as a lyophilized lipopolysaccharide to be reconstituted with LAL Reagent Water. See Example 2.

The methods of the invention provide a simple and rapid method for detection and measurement of the bacterial cell-wall toxin endotoxin and fungal cell-wall toxin 1,3-β-D-glucan. These can be measured by means of the *Limulus* Amoebocyte Lysate (LAL) clotting response to these toxins in solution. The sensitivity of NMR relaxation rates to clot formation in solution can be used to detect and measure endotoxin by means of the LAL gelation reaction. When the LAL polymerizes, water diffusion is effected, thereby altering the measured NMR relaxation values. The methods and devices of the invention can be used to quickly and efficiently assess endotoxin levels in a sample.

Clotting Initiation

For performing the methods of the invention, clotting may be initiated using a Factor-C containing reagent. A suitable Factor C-containing reagent may be a horseshoe crab amebocyte lysate conventionally used for the *Limulus* test. Such a horseshoe crab amebocyte lysate is not particularly limited as long as it is derived from, for example, hemocytes of horseshoe crabs belonging to the *Limulus* sp., the *Tachypleus* sp. or the *Carcinoscorpius* sp., and it can produce the clotting enzyme via a reaction with endotoxin. Therefore, a commercially available *Limulus* reagent (LAL reagent), or a *Limulus* reagent (LAL reagent) provided in a kit for endotoxin measurement can be suitably used.

It is also possible to use a recombinant Factor C derived from a recombinant gene prepared based on all or a part of the horseshoe crab Factor C gene. A suitable example of the recombinant Factor C may be the recombinant Factor C provided in the commercially available PyroGene rFc (manufactured by Lonza Walkersville and Inc., distributed by Daiichi Pure Chemicals Co., Ltd.). Alternatively, the recombinant Factor C may be obtained by preparing an expression vector having the horseshoe crab Factor C gene inserted thereinto according to a known genetic engineering method, introducing the vector into appropriate host cells to achieve expression of a recombinant protein, and purifying the protein.

The methods of the invention can be performed using a reduced amount of C-containing reagent. When the horseshoe crab amebocyte lysate conventionally used in the *Limulus* test (for example, a commercially available *Limulus* reagent) as the Factor C-containing reagent, the amount used with the methods of the invention can be about 10% to 50% of the typical amount otherwise used. This is because of the increased sensitivity of the assay of the invention. About 10% to 50% of the typical amount is equivalent to approximately 0.375 to 2.2 mg/mL of protein derived from horseshoe crab amebocyte lysate.

Signal Acquisition and Processing

Standard radiofrequency pulse sequences for the determination of nuclear resonance parameters are known in the art, for example, the Carr-Purcell-Meiboom-Gill (CPMG) is traditionally used if relaxation constant $T_2$ is to be determined. Optimization of the radiofrequency pulse sequences, including selection of the frequency of the radiofrequency pulses in the sequence, pulse powers and pulse lengths, depends on the system under investigation and is performed using procedures known in the art.

Nuclear magnetic resonance parameters that can be obtained using the methods of the present invention include but are not limited to T1, T2, T1/T2 hybrid, $T_{1rho}$, $T_{2rho}$ and $T_2^*$. Typically, at least one of the one or more nuclear resonance parameters that are obtained using the methods of the present invention is spin-spin relaxation constant T2.

As with other diagnostics and analytical instrumentation, the goal of NMR-based diagnostics is to extract information from a sample and deliver a high-confidence result to the user. As the information flows from the sample to the user it typically undergoes several transformations to tailor the information to the specific user. This can be achieved by processing the NMR relaxation signal into one or more series of component signals representative of the different populations of water molecules present, e.g., in a sample that is undergoing endotoxin-induced clotting. For example, NMR relaxation data, such as T2, can be fit to a decaying exponential curve defined by the following equation:

$$f(t) = \sum_{i=1}^{n} A_i \exp(-t/T(i)) \tag{3}$$

where f(t) is the signal intensity as a function of time, t, A, is the amplitude coefficient for the ith component, and (T), the decay constant (such as T2) for the ith component. For relaxation phenomenon discussed here the detected signal is the sum of a discrete number of components (i=1, 2, 3, 4 . . . n). Such functions are called mono-, bi-, tri-, tetra- or multi-exponential, respectively. Due to the widespread need for analyzing multi-exponential processes in science and engineering, there are several established mathematical methods for rapidly obtaining estimates of $A_i$ and $(T)_i$ for each coefficient. Methods that have been successfully applied and may be applied in the processing of the raw data obtained using the methods of the present invention include Laplace transforms, algebraic methods, graphical analysis, nonlinear least squares (of which there are many flavors), differentiation methods, the method of modulating functions, integration method, method of moments, rational function approximation, Padé-Laplace transform, and the maximum entropy method (see Istratov, A. A. & Vyvenko, O. F. Rev. Sci. Inst. 70:1233 (1999)). Other methods, which have been specifically demonstrated for low field NMR include singular value decomposition (Lupu, M. & Todor, D. Chemometrics and Intelligent Laboratory Systems 29:11 (1995)) and factor analysis.

There are several software programs and algorithms available that use one or more of these exponential fitting methods. One of the most widely cited sources for exponential fitting programs are those written and provided by Stephen Provencher, called "DISCRETE" and "CONTIN" (Provencher, S. W. & Vogel, R. H. Math. Biosci. 50:251 (1980); Provencher, S. W. Comp. Phys. Comm. 27:213 (1982)). Discrete is an algorithm for solving for up to nine discrete components in a multi-component exponential curve. CONTIN is an algorithm that uses an inverse Laplace transform to solve for samples that have a distribution of relaxation times. Commercial applications using multiexponential analyses use these or similar algorithms. In fact, Bruker minispec uses the publicly-available CONTIN algorithm for some of their analysis. For the invention described here, the relaxation times are expected to be discrete values unique to each sample and not a continuous distribution, therefore programs like CONTIN are not needed although they could be used. The code for many other exponential fitting methods are generally available (Istratov, A. A. & Vyvenko, O. F. Rev. Sci. Inst. 70:1233 (1999)) and can be used to obtain medical diagnostic information according to the methods of the present invention. Information is available regarding how the signal to noise ratio and total sampling time relates to the maximum number of terms that can be determined, the maximum resolution that can be achieved, and the range of decay constants that can be fitted. For a signal to noise ratio of $\sim 10^4$ the theoretical limit as to the resolution of two decay constants measured, independent of the analytical method, is a resolution=$(T_i/T_{i+1})$ of >1.2 (Istratov, A. A. & Vyvenko, O. F. Rev. Sci. Inst. 70:1233 (1999)). Thus it is believed that the difference between resolvable decay constants scales with their magnitudes, which is not entirely intuitive and is unlike resolution by means of optical detection. The understanding of the maximum resolution and the dependence on resolution on the signal-to-noise ratio will assist in assessing the performance of the fitting algorithm.

Further the methods of the invention can be used on a benchtop NMR relaxometer, benchtop time domain system, or NMR analyzer (e.g., ACT, Bruker, CEM Corporation, Exstrom Laboratories, Quantum Magnetics, GE Security division, Halliburton, HTS-111 Magnetic Solutions, MR Resources, NanoMR, NMR Petrophysics, Oxford Instruments, Process NMR Associates, Qualion NMR Analyzers, SPINLOCK Magnetic Resonance Solutions, or Stelar, Resonance Systems).

The CPMG pulse sequence used to collect data with a T2reader is designed to detect the inherent T2 relaxation time of the sample. Typically, this is dictated by one value, but for samples containing a complex mixture of states (e.g., a sample undergoing a clotting process or dissolution process) in a slow-exchange regime, a distribution of T2 values can be observed. In this situation, the signal obtained with a CPMG sequence is a sum of exponentials. One solution for extracting relaxation information from a T2reader output is to fit a sum of exponentials in a least-squares fashion. Practically, this requires a priori information on how many functions to fit. A second solution is to use the Inverse Laplace transform (ILT) to solve for a distribution of T2 values that make up the exponential signal observed. Again, the results of the CPMG sequence S(t), is assumed to be the sum of exponentials $$S(t) = \sum_i A_i e^{-t/T2_i} \quad (4)$$

Where $A_i$ is the amplitude corresponding to the relaxation time constant $T2_i$. If, instead of a discrete sum of exponentials, the signal is assumed to be a distribution of T2 values, the sum over states can be represented by $$S(t) = \int_0^\infty A(1/T1)e^{-t/T2}d(1/T2) \quad (5)$$

This has the same functional form as the ILT $$F(t) = \int_0^\infty A(s)e^{-st}ds \quad (6)$$

and can be treated as such. The ILT of an exponential function requires constraints to solve. A few methods that can be used to impose constraints are CONTIN, finite mixture modeling (FMM), and neural networks (NN). An inverse Laplace transform may also be used in the generation of a 3D data set. A 3D data set can be generated by collecting a time series of T2 decay curves and applying an inverse Laplace transform to each decay curve to form a 3D data set. Alternatively, a 2D inverse Laplace transform can be applied to a pre-assembled 3D data set to generate a transformed 3D data set describing the distribution of T2 times.

In a heterogeneous environment containing two phases, several different exchange regimes may be operative. In such an environment having two water populations (a and b), $r_a$ and $r_b$ correspond to the relaxation rates of water in the two populations; $f_a$ and $f_b$ correspond to the fraction of nuclei in each phase; $r_a$ and $r_b$ correspond to residence time in each phase; and $a=(1/\tau_a)+(1/\tau_b)$ corresponds to the chemical exchange rate. The exchange regimes can be designated as: (1) slow exchange: if the two populations are static or exchanging slowly relative to the relaxation rates $r_a$ and $r_b$, the signal contains two separate components, decaying with time constants $T_{2a}$ and $T_{2b}$; (2) fast exchange: if the rate for water molecules exchanging between the two environments is rapid compared to $r_a$ and $r_b$, the total population follows a single exponential decay with an average relaxation rate ($r_{av}$) given by the weighted sum of the relaxation rates of the separate populations; and (3) intermediate exchange: in the general case where there are two relaxation rates $r_1$ and $r_2$ with $r_1$ equal to $r_a$ in the slow exchange limit $r_a<r_b$, $Amp_1+Amp_2=1$, and where $r_{1,2}$ goes to the average relaxation rate in the fast exchange limit, equations 7, 8, 9, and 10 may be applied:

$$r_1 = (1/2)(r_a + r_b + a) - (1/2)\sqrt{(r_b - r_a + a)^2 - 4af_b(r_b - r_a)} \quad (7)$$

$$r_2 = (1/2)(r_a + r_b + a) + (1/2)\sqrt{(r_b - r_a + a)^2 - 4af_b(r_b - r_a)} \quad (8)$$

$$Amp_1 = \frac{r_2 - r_{av}}{r_2 - r_1} \quad (9)$$

$$Amp_2 = \frac{r_{av} - r_1}{r_2 - r_1} \quad (10)$$

The invention also features the use of a pulsed field gradient or a fixed field gradient in the collection of relaxation rate data. The invention further features the use of the techniques of diffusion-weighted imaging (DWI) as described in Vidmar et al. (Vidmar et al., *NMR Biomed.* 23: 34-40 (2010)), which is herein incorporated by reference, or any methods used in porous media NMR (see, e.g, Bergman et al., *Phys. Rev. E* 51: 3393-3400 (1995), which is herein incorporated by reference).

Magnetic Particles

The methods of the invention can be carried out in the presence of a paramagnetic agent (i.e., gadolinium, manganese, magnetic particles, etc.) added, e.g., to the sample prior to initiating clotting. The paramagnetic reagent can be used to shorten the relaxation times of the water molecules, permitting the data acquisition to proceed with shorter dwell times.

The magnetic particles that can be used in the methods of the invention include those described, e.g., in U.S. Pat. No. 7,564,245 and U.S. Patent Application Publication No. 2003-0092029, each of which is incorporated herein by reference. The particles have high relaxivity owing to the superparamagnetism of their iron, metal oxide, or other ferro or ferrimagnetic nanomaterials. Iron, cobalt, and nickel compounds and their alloys, rare earth elements such as gadolinium, and certain intermetallics such as gold and vanadium are ferromagnets can be used to produce superparamagnetic particles. The magnetic particles can be monodisperse (a single crystal of a magnetic material, e.g., metal oxide, such as superparamagnetic iron oxide, per magnetic particle) or polydisperse (e.g., a plurality of crystals per magnetic particle). The magnetic metal oxide can also comprise cobalt, magnesium, zinc, or mixtures of these metals with iron. The magnetic particles typically include metal oxide crystals of about 1-25 nm, e.g., about 3-10 nm, or about 5 nm in diameter per crystal. The magnetic particles can also include a polymer component in the form of a core and/or coating, e.g., about 5 to 20 nm thick or more. The overall size of the magnetic particles can be, e.g., from 20 to 50 nm, from 50 to 200 nm, from 100 to 300 nm, from 250 to 500 nm, from 400 to 600 nm, from 500 to 750 nm, from 700 to 1,200 nm, from 1,000 to 1,500 nm, or from 1,500 to 2,000 nm. Magnetic particle size can be controlled by adjusting reaction conditions, for example, by using low temperature during the neutralization of iron salts with a base as described in U.S. Pat. No. 5,262,176. Uniform particle size materials can also be made by fractionating the particles using centrifugation, ultrafiltration, or gel filtration, as described, for example in U.S. Pat. No. 5,492,814. Magnetic particles can also be synthesized according to the method of Molday (Molday, R. S. and D. MacKenzie, "Immunospecific ferromagnetic iron-dextran reagents for the labeling and magnetic separation of cells," J. Immunol. Methods, 52:353 (1982)), and treated with periodate to form aldehyde groups. The aldehyde-containing magnetic particles can then be reacted with a diamine (e.g., ethylene diamine or hexanediamine), which will form a Schiff base, followed by reduction with sodium borohydride or sodium cyanoborohydride. The magnetic particles can be formed from a ferrofluid (i.e., a stable colloidal suspension of magnetic particles). For example, the magnetic particle can be a composite of multiple metal oxide crystals of the order of a few tens of nanometers in size and dispersed in a fluid containing a surfactant, which adsorbs onto the particles and stabilizes them, or by precipitation, in a basic medium, of a solution of metal ions. Suitable ferrofluids are sold by the company Liquids Research Ltd. under the references: WHKS1S9 (A, B or C), which is a water-based ferrofluid comprising magnetite ($Fe_3O_4$), having particles 10 nm in diameter; WHJS1 (A, B or C), which is an isoparaffin-based ferrofluid comprising particles of magnetite ($Fe_3O_4$) 10 nm in diameter; and BKS25 dextran, which is a water-based ferrofluid stabilized with dextran, comprising particles of magnetite ($Fe_3O_4$) 9 nm in diameter. Other suitable ferrofluids for use in the systems and methods of the invention are oleic acid-stabilized ferrofluids available from Ademtech, which include ca. 70% weight $\alpha$-$Fe_2O_3$ particles (ca. 10 nm in diameter), 15% weight octane, and 15% weight oleic acid. The magnetic particles are typically a composite including multiple metal oxide crystals and an organic matrix, and having a surface decorated with functional groups (i.e., amine groups or carboxy groups) for linking binding moieties to the surface of the magnetic particle. For example, the magnetic particles useful in the methods of the invention include those commercially available from Dynal, Seradyn, Kisker, Miltenyi Biotec, Chemicell, Anvil, Biopal, Estapor, Genovis, Thermo Fisher Scientific, JSR micro, Invitrogen, and Ademtech, as well as those described in U.S. Pat. Nos. 4,101,435; 4,452,773; 5,204,457; 5,262,176; 5,424,419; 6,165,378; 6,866,838; 7,001,589; and 7,217,457, each of which is incorporated herein by reference. The methods of the invention can be performed in the presence of particles that contain multiple superparamagnetic iron oxide cores (5-15 nm diameter) within a single larger polymer matrix or ferrofluid assembly (100 nm-1200 nm total diameter, such as particles having an average diameter of 100 nm, 200 nm, 250 nm, 300 nm, 500 nm, 800 nm, or 1000 nm), or by using a higher magnetic moment materials or particles with higher density, and/or particles with higher iron content.

Uses

The NMR-based methods of the invention described herein may be used in a variety of applications where a substance or mixture of substances is undergoing testing for endotoxin contamination.

The methods of the invention can be performed in conjunction with other systems, devices, and/or methods for the rapid detection of analytes or an analyte concentration in a sample. For example, the methods of the invention can be performed in conjunction with the systems, devices, and methods described in PCT Publication No. PCT/US2011/56936, filed Oct. 19, 2011, and incorporated herein by reference, which can include one or more of the following: (i) assay for endotoxin in water, diasylate, pharmaceutical preparations, or biopharmaceutical preparations; (ii) end-product testing of human injectable or animal injectable fluids (including drugs, medicaments, solutions), or medical devices; (iii) assay for endotoxin in raw materials used in production, including water; (iv) assay for endotoxin for in-process monitoring of endotoxin levels for any medical procedure; (v) assay biological samples (e.g., blood, sweat, tears, urine, saliva, semen, serum, plasma, cerebrospinal fluid (CSF), feces, vaginal fluid or tissue, sputum, nasopharyngeal aspirate or swab, lacrimal fluid, mucous, or epithelial swab (buccal swab), tissues, organs, bones, teeth, or tumors, among others); (vi) monitor an environmental condition (e.g., plant growth hormone, insecticides, man-made or environmental toxins, nucleic acid sequences that are important for insect resistance/susceptibility, algae and algae by-products), (vi) in a bioremediation program; for use in farming plants or animals, or to identify environmental hazards; and/or (viii) to detect and monitor biowarfare or biological warfare agents (e.g., ricin, Salmonella typhimurium, botulinum toxin, aflatoxin, mycotoxins, Francisella tularesis, small pox, anthrax). For example, the methods of the invention can be performed in conjunction with assays designed to identify pathogens insensitive to endotoxin testing, or to identify the species of pathogen present in a given sample.

Lonza LAL reagents were used to confirm the performance of the gel clot and/or turbidimetric assays in response to known amounts of endotoxin. The LAL reagents and accessories used to perform the assays are listed in Table 1.

TABLE 1

| Product Name | Description | Part No. | Sensitivity (EU/ml) | Time to results |
|---|---|---|---|---|
| PYROGENT ™ | Gel clot LAL kit | E194-03 | 0.03 | 60 min |
| PYROGENT ™ | Gel clot LAL kit | E194-125 | 0.125 | 60 min |
| PYROGENT ™ | Gel clot LAL kit | E209-06 | 0.06 | 60 min |
| PYROGENT ™ | Gel clot LAL kit | E209-25 | 0.25 | 60 min |
| PYROGENT ™-5000 | Kinetic turbidimetric LAL kit | T50-300 | 0.01 | 30-45 min |
| Endotoxin | USP Reference Standard | E700 | n/a | n/a |
| LAL Reagent Water | <0.005 EU/ml | W50-640 | n/a | n/a |
| Pyrogen-free tips | Pipette tips, 2 to 200 ul | 25-415 | n/a | n/a |
| Pyrogen-free tips | Pipette tips, 50 to 1000 ul | 25-417 | n/a | n/a |
| Pyrogen-free tubes | 13 × 100 mm dilution tubes | N207 | n/a | n/a |
| Pyrogen-free tubes | 10 × 75 mm reaction tubes | N205 | n/a | n/a |

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1: Detection of Bacterial Endotoxin

The methods and device of the invention are used to detect bacterial endotoxin, i.e., cell wall material from gram-negative bacteria. Endotoxin is capable of causing high fevers in humans, and, consequently, injectable drugs and medical devices that contact the blood are frequently tested for the presence of endotoxin. A clotting-based assay for detecting endotoxin relies upon the reaction between bacterial endotoxin and a specific lysate used in the assay. A lysate derived from the circulating amebocytes of the horseshoe crab *Limulus polyphemus* is a particular lysate that can be used. In the assay, the lysate is introduced to a sample to be tested for the presence of endotoxin. If a gel is formed, via a clotting process, endotoxin is deemed to be present. The formation and properties of such a gel are monitored by any of the NMR-based methods described herein.

Example 2: Detection of Endotoxin by Magnetic Relaxation

The goal of the study is to determine the applicability of magnetic relaxation as a means for detecting endotoxin-induced clot formation. This study utilizes Lonza *Limulus* Amebocyte Lysate (LAL) reagent(s). General protocols for performing a gelation endotoxin assay (by observation or optical detection) are depicted in FIG. 1.

The clotting cascade of Horseshoe crabs is a primitive defense mechanism to infection by bacteria and fungi. In response to the Lipopolysaccharide (LPS) molecules found on the cell wall of gram negative bacteria, an orchestrated cascade of events will direct a gelation reaction ultimately engulfing the invading organism. This well characterized clotting cascade has been exploited in the Pharmaceutical Industry as a surrogate assay to detect the presence of endotoxin or LPS, a known pyrogen.

A demonstration of assay sensitivity and clotting time (and turgor) was used to establish a baseline for comparison. The same reagents were then be used to evaluate to potential application of magnetic relaxation as a means for the detection of the endotoxin-induced clotting reaction.

The endotoxin was reconstituted in 5 mL LAL reagent water (LRW) (results in 2000 EU/ml solution) and vortexed 30 minutes. A series of dilutions was performed to generate standard endotoxin solutions (i.e., from 200 EU/mL solution to 0.001 EU/mL solution).

The LAL reagent was reconstituted in LAL reagent water, and the contents swirled gently until dissolution.

Each tube was prepared by adding the LAL reagent solution to the test sample containing a predetermined amount of endotoxin (or a blank).

The reaction was monitored in a T2 magnetic reader, holding test temperature constant (+/−1° C.) throughout assay. All T2MR data was processed using the following signal acquisition settings and signal processing algorithm: all data was acquired on two T2MR readers. Signal acquisition settings: 45 us tau, 6 sec recycle delay, 6 sec total echo time, 300 T2 measurements every ~14 seconds. Signal processing settings: smoothing function of 16 or 22 moving boxcar average, % DT2 normalization to either the T2 value at 2 min, 5 min, or the maximum T2 value. The "time to clot" was determined at threshold changes in T2 of 0.2%, 0.5% or 2%.

Results

For the assay conducted in the T2 instrument, a linear response to the changes in endotoxin concentration were observed, as was a reasonable separation between the lowest standard and the negative control is desired.

Figure 2:
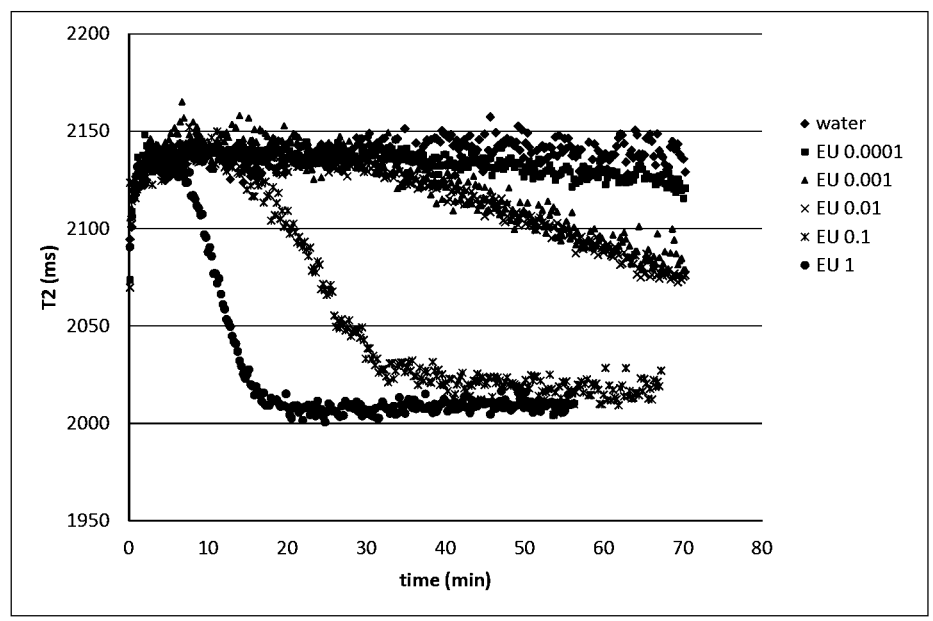
FIG. 2 is a graph depicting the T2 relaxation rate of water as a function of time following the initiation of the clotting reaction by addition of varying levels of endotoxin standard to the LAL reagent (see Example 2). An increase in the change is the T2 relaxation rate of water over time was observed with increasing levels of endotoxin. The T2 relaxation rate has a dose-dependent response to endotoxin levels and adequate resolution of the positive samples from the zero as low as 0.005 EU/mL. The data was collected on two readers over the period of 3.5 hours.
Figure 3:
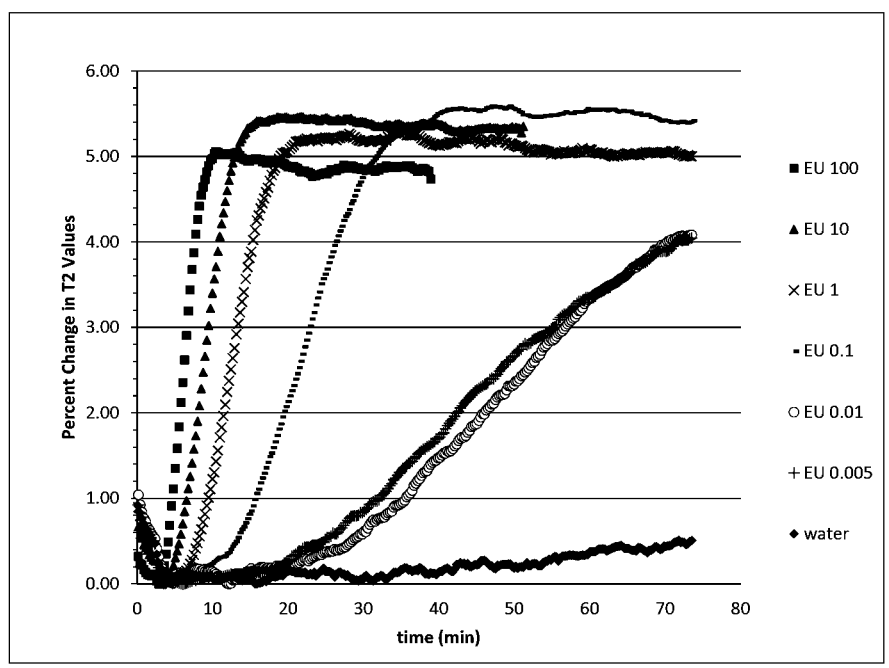
FIG. 3 is a graph depicting the percent change in the T2 values as a function of time following the initiation of the clotting reaction by addition of varying levels of endotoxin standard to the LAL reagent (see Example 2). The percent change in the T2 value at a predetermined time point can be used to determine the concentration of endotoxin in a sample.
Figure 5:
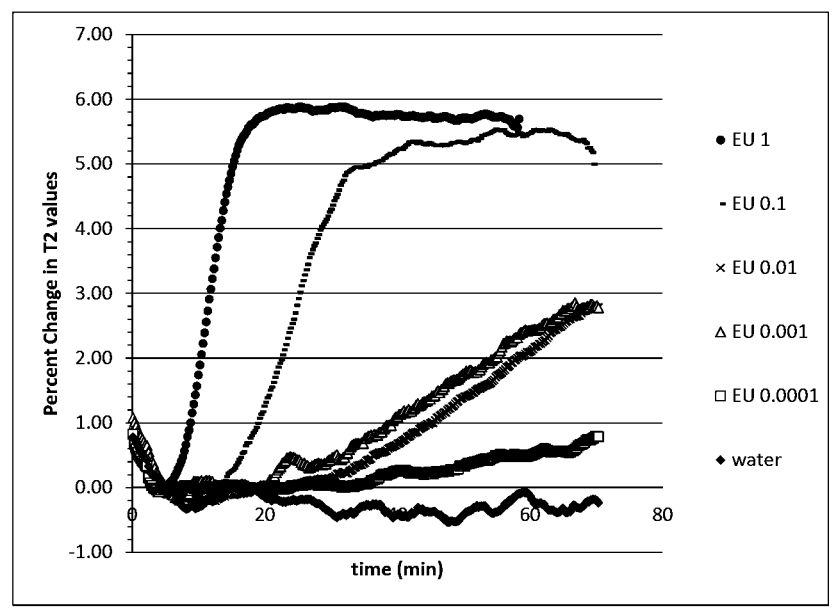
FIG. 5 is a graph depicting the T2 relaxation rate of water as a function of time following the initiation of the clotting reaction by addition of varying levels of endotoxin standard (down to 0.0001 EU) to the LAL reagent (see Example 2). The T2 relaxation rate has a dose-dependent response to endotoxin levels and adequate resolution of the positive samples from the zero as low as 0.0001 EU/mL.

An increase in the change is the T2 relaxation rate of water over time was observed with increasing levels of endotoxin (see FIGS. 2, 3, and 5). The T2 relaxation rate has a dose-dependent response to endotoxin levels and adequate resolution of the positive samples from the zero to as low as 0.005 EU/mL (see FIG. 2) or 0.0001 EU/mL (see FIG. 5).

The data can be presented as the percent change in the T2 values as a function of time following the initiation of the clotting reaction by addition of varying levels of endotoxin standard to the LAL reagent (see FIG. 3). The percent change in the T2 value at a predetermined time point can be used to determine the concentration of endotoxin in a sample.

Figure 4:
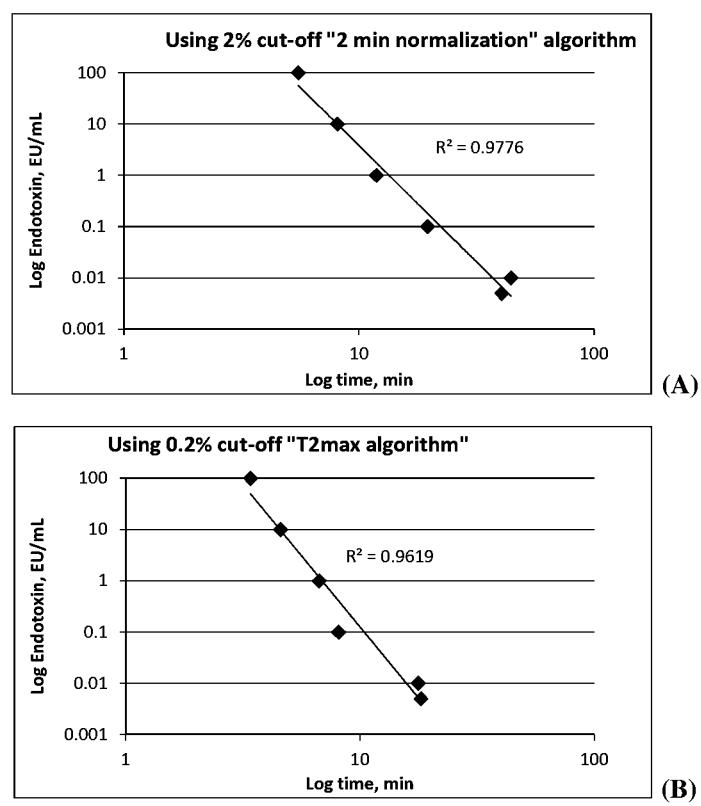
FIGS. 4A and 4B are plots depicting the correlation between endotoxin level versus the clotting time for a predetermined percent change in T2 value (see Example 2).

We observed correlation between endotoxin level versus the clotting time at for a predetermined percent change in T2 value (see FIGS. 4A and 4B). FIG. 4A depicts the correlation for a 2% change in T2. FIG. 4B depicts the correlation for a 0.2% change in T2. The strong correlation observed for small changes in T2 permit rapid detection of endotoxin in a sample. These results are provided in Table 2, below.

TABLE 2

| Endotoxin level, EU/mL | Time at 2% dT2, min | Time at 0.2% dT2, min |
|---|---|---|
| 100 | 5.52 | 3.41 |
| 10 | 8.1 | 4.58 |
| 1 | 11.86 | 6.69 |
| 0.1 | 19.62 | 8.1 |
| 0.01 | 44.26 | 17.74 |
| 0.005 | 40.51 | 18.21 |

CONCLUSIONS

Our results demonstrate that the present method can have the following advantages: (i) improved sensitivity in comparison to turbidometric measurements (0.0001 EU/mL versus 0.01 EU/mL); (ii) a shorter time to produce a result in comparison to turbidometric measurements (~17 minutes using T2 signal versus ~30 minutes using turbidometric methods); and (iii) a reduction in LAL reagent used in the assay (~20 μL LAL reagent using T2 signal versus ~100 μL LAL reagent using turbidometric methods).

The magnetic relaxation approach for endotoxin detection provides a sensitivity advantage because the measurement probe is the water molecules in the sample. When diffusion properties of water change, then the T2 signal changes. This method of measurement can be highly sensitive due to the sensitivity of water to changes in the solution at the molecular level. It is believed that this is the underlying principle for the superior sensitivity of magnetic relaxation detection for endotoxin, as compared to optical turbidometric measurements that require a significant fraction of the solution to scatter or absorb light.

Our other advantages include the robustness of the detector to additives that might interfere with optical detection methods (i.e., samples that alter the optical clarity of the solution will not interfere with our detector).

Using the methods of the invention, detection times were more than 50% shorter and sensitivity improved by 100× in comparison to optical methods using the same reagents.

Figure 6:
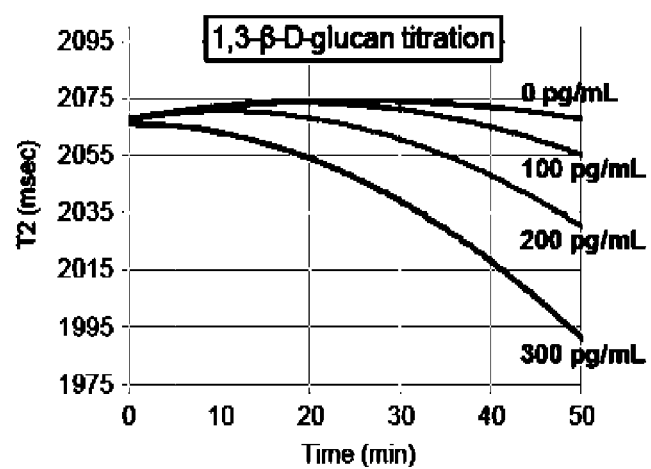
FIG. 6 is a graph depicting the T2 relaxation rate of water as a function of time following the initiation of the clotting reaction by addition of varying amounts of 1,3-β-D-glucan (see Example 3). The resulting dose response curve for 1,3-β-D-glucan in buffer shows that 100 pg/mL of 1,3-β-D-glucan was detected in less than 45 minutes. A boxcar smoothing function was applied to the T2 signal.

Example 3: Dose Response Curve for 1,3-β-D-Glucan 1,3-β-D-glucan is a component of the fungal cell wall and can be used for systematic screening and identification of significant fungal infections. PYROGENT-5000 reagents (Lonza) were used (as described in Example 2) with detection methods of the invention to generate a dose response curve for 1,3-β-D-glucan in buffer. The results are depicted in FIG. 6, demonstrating that 100 pg/mL of 1,3-β-D-glucan was detected in less than 45 minutes. A boxcar smoothing function was applied to the T2 signal. In comparison to endotoxin detection, smaller T2 changes were observed. This smaller change in T2 was likely due to the lack of specificity of the LAL reagent for the clotting initiator. Sensitivity and specificity can be improved with assay optimization.

Example 4: Data Extraction Algorithms for Interpreting Clotting in a Sample in the Slow Exchange Rate Regime For slow exchange rate regime samples, the clotting process can be monitored as described in Example 2, and the data output from the T2reader can be processed using a three-step method of performing a bi-exponential fit, plotting and checking, feature extraction, T2 signature curves, relaxation spectra, and 3D plot of water populations in a clot (all described below).

Bi-Exponential Fit

The curves can be fitted to a bi-exponential equation using start points (e.g., seeds) for AmpA, AmpB, T2A, and T2B with fixed seeds used for the first five time points. The seed for the sixth time point can be obtained from the average of the first five time points. Generally, time points can be seeded with output from the previous time point. Negative values for parameters can be not allowed. Alternatively, the data can be fit initially in the middle of the time series, working similarly to the ends. The goodness-of-fit term can be computed by taking the sum of squares of the fit residuals, excluding non-negative values, called SSE. The parameters AmpA, AmpB, T2A, and T2B can be binned into their respective categories to create a text file.

Plotting and Checking

The fits that do not meet the SSE criteria can be flagged and removed. A simple smoothing function based on local regression using weighted LLS and 1 degree polynomials can be performed and outlier data was discarded. Each fit parameter can be plotted versus time (smoothed and unsmoothed).

Extract Features

The plotted curves can be measured to extract the values associated with clotting behaviors, such as clotting time. Data extraction can be carried out using any of a variety of methods known in the art. For example, metrics can be derived from the curve shape of the resulting data and/or calculated from the value of one or more NMR parameters.

T2 Signature Curves

NMR data can be processed to create a T2 signature curve displaying distinct signals (i.e. maxima) that represent individual water populations within a sample. The T2 signature curves are created by applying a mathematical transform (e.g., a Laplace transform or inverse Laplace transform) to a decay curve associated with T2 at a time point during a clotting event.

T1 Relaxation Measurements

In addition to being able to measure T2 measurements, T2readers can be configured to measure T1 measurements. T1 measures different physical properties of the hydrogen atom spin system in the sample. Therefore, T1 data provides alternative and complementary information about endotoxin clotting compared to T2 data. While conventional T1 measurements are time consuming (2-3 minutes) due to the step-wise nature of acquiring the T1 signal, a z-refocused echo (ZRE) method can be used to acquire T1 within less than 5 seconds. T1 relaxation measurements can be used in the endotoxin detection assays of the invention.

T1/T2 Hybrid Detection Methods

T1/T2 hybrid detection methods are known in the art (Edzes, *J. Magn. Reson.* 17: 301-313, 1975; Sezginer et al., *J. Magn. Reson.* 92: 504-527, 1991, which are hereby incorporated by reference). These methods and related methods may be used in the endotoxin detection assays of the invention.

T1 is typically sampled by means of an inversion-recovery sequence. Inversion recovery sequences can take several minutes to acquire depending on the precision of the measured relaxation time that the user wants to achieve, which is dictated by the number of data measurements used in the pulse sequence. The details of the inversion recovery sequence will not be described here, as they can be looked up in any standard NMR textbook.

A T1ZRE pulse sequence allows for the measurement of T1 over the time required for the magnetization to completely relax. (~3-5×T1). This is achieved by inverting the magnetization with a 180° pulse and then sampling the magnetization while the magnetization returns to equilibrium by measuring its magnitude and returning it to its original −z position with a series of pulses.

The time that it takes to sample the magnetization is called $\tau_c$, and the time between samplings is $\tau_r$. The time after the start of $\tau_c$ until the actual measurement is $\tau_m$. The measured relaxation constant is a combination of $R_2$ and $R_1$ and is referred to as $R_{12}$. The three terms are related by $$R_{12} = (1-P)R_1 + pR_2 \quad (11)$$

where $p = \tau_c/\tau_r$. From this relation, one can see that R12 goes to R1 when p goes to 0.

$\tau_r$ will depend on the total number of points and the total duration of the measurement. For T2COAG measurements, it was 30 points over ~3 seconds for a $\tau_r$ of 100 milliseconds. The $\tau_c$ term can be calculated from the pulse sequence and is essentially equivalent to 3×tau or 750 μs. Accordingly, the p term is equal to 0.0075 and the measured relaxation, or hybrid, T1/T2 (hT12) term should primarily be T1. Sezginer et al. provide a simple equation to derive the T1 measurement from the hT12 signal, which is $$\frac{1}{T_1^{meas}} = \frac{T_b}{T_1(4t_{cp} + T_b)} + \frac{4t_{cp}}{T_2(4t_{cp} + T_b)} \quad (12)$$

where $T_1^{meas}$ is hT12, $T_1$ is T1, $T_b$ is the duration between the two measurements, $t_{cp}$ is half of the inter-echo delay or tau, and $T_2$ is the measured T2 time.

The above description is simply illustrative of how this hybrid relaxation time can be measured. There are other pulse sequences that can be used to measure hybrid relaxation constants and derive T1 in a rapid fashion.

Regardless of the pulse sequence used, the inventive concept is directed to rapid acquisition of magnetic resonance relaxation measurements. Other types of magnetic resonance pulse sequences can be used to monitor the bulk hydrogen signal in the sample during coagulation. Examples include T2, T1, T1/T2 hybrid times, their inverse terms of R2, R1, R12, and pulsed NMR measurements commonly used for materials analyses on relaxometers such as free induction decay (FID) based analyses, fast Fourier transform based analyses (FFT). FID analysis commonly discriminates between rapidly decaying signals and slowly decaying signals. The intensities of these two signals can be compared, as can their decay constants. These pulse sequences have been commonly used for fat analysis, fat content and solid to liquid ratio, solid fat to liquid ratio, hydrogen content determination, oil content, solids content, and total fat content determinations, oil water emulsions, and fat and moisture determinations. Similar real-time or kinetic measurements can be performed with those NMR parameters on samples that are undergoing an endotoxin-induced clotting reaction.

Alternative relaxation measurements are attractive to provide: (1) more information of the clotting process; (2) specific information not captured by the T2 measurement; and (3) normalization for factors that both T2 and the new parameter are sensitive to. To describe point 3 more, if, for example, T1 measurements are sensitive to variations sample to sample but T1 does not contain the coagulation information then there should be an algorithm to use the T1 curve to "subtract out" the part of the T2 signal that arises from undesired sensitivities in the samples.

Database of Signature Curves

The invention features data processing tools to transform the raw relaxation NMR data into a format that provides signature curves characteristic of a clotting process. Possible transforms include the Laplace or inverse Laplace transform (ILT). The data for each T2 measurement may be transformed from the time dimension where signal intensity is plotted verses time to a "T2 relaxation" dimension. The ILT provides not only information about the different relaxation rates present in the sample and their relative magnitudes but also reports on the breadth of distribution of those signals.

Each acquired T2 relaxation curve has a corresponding two dimensional signature that maps all of the different populations of water, or different T2 relaxation environments, that water is experiencing in the sample. These curves can be compiled to form a 3D data set by stacking the plots over the duration of the clotting time dimension. This generates a 3D surface that shows how the different populations of water change as a function of time.

The data gathered using the methods of the invention can be represented using 3D plots generated from different NMR parameters. Additional dimensions can be added by looking at specific patient types or clotting curve types. Data reduction methods can be used to simplify the complex information that is available. Such techniques as principal component analyses (PCA), automated feature extraction methods, or other data handling methods can be used. Ideally, a library of signatures, 2D, and 3D plots can be generated for a wide variety of clinical conditions. For example, two dimensional (intensity versus T2 value or T2 value versus time) or three dimensional representations (intensity versus T2 value versus time). The T2 values in the two- or three dimensional representation may be replaced with or compared to other NMR signals such as T1, T1/T2 hybrid, $T_{1rho}$, $T_{2rho}$ and $T_2^*$.

Alternatively, an endotoxin-induced clotting process within a sample is assessed by an NMR parameter extracted from one or more free induction decay (FID) signals obtained from the sample. For example, an NMR parameter can be extracted from the signal to noise ratio of an FID, from a comparison of an FID to a predetermined threshold, or from the integration of an FID. The NMR parameters obtained by the method can be used to characterize the clotting process, improve sensitivity, or reduce the amount of time needed to produce a test result.

T2 relaxation spectra can be used to identify and monitor different populations of water in a sample undergoing clotting.

3D Data Plots and Dashboard Displays 3D representations of the T2 data in a sample undergoing a clotting process may be generated using the methods of the invention. In certain embodiments, the dimensions of the generated 3D plots correspond to a relaxation time (e.g., T2 or 1/T2) dimension, an intensity or amplitude dimension, and a time dimension. The time dimension represents the time over which the clotting process has proceeded or is proceeding. The 3D plots obtained from endotoxin-induced clotting can exhibit a variety of topographical features that correspond with separate water populations in different physical and/or chemical environments within the sample. The 3D plots and the data used to generate the 3D plots may be mined for biomarkers or clotting behaviors associated with the sample. The 3D plots or the data used to generate the 3D data plots may also be used to discover new biomarkers.

The 3D data associated with a 3D plot of a clotting sample can be used to generate a Dashboard Display featuring a variety of biomarkers and/or clotting behaviors either in real time or after the clotting process has concluded. A similar dashboard display can be generated using the methods of the invention for an endotoxin assay. The information contained within the different topographical features and water populations evident in the 3D plot may be associated with particular biomarkers and clotting behaviors. A variety of methods can be used to extract the biomarkers or clotting behaviors from the 3D data set. For example, the slope or curvature of a topographical feature of a 3D plot may be correlated with a clotting behavior. A cross-section of a 3D plot may also be used to calculate a clotting behavior. A cross-section of a 3D plot showing T2 time as a function of intensity at a given time (a T2 relaxation spectrum) depicts the various water populations present in a sample at a given time. The features of a T2 relaxation spectrum can be mined for a range of clotting behaviors. The integration of a particular topographical feature, such as the volume of a particular feature, or curve from a cross-section of a 3D plot may also be useful in establishing a clotting behavior (e.g. clot strength). Clotting behaviors may also be extracted through the integration of a range of T2 relaxation spectra collected at sequential or disparate time points.

Alternatively, the 3D plots can be used to identify a feature characteristic of clot behavior. The feature can be one that is measured without 3D analysis, such as via pulse sequence for selectively monitoring a water population having an average T2 relaxation rate of about 400 milliseconds or 1,000 milliseconds at a particular time post clot initiation. Optionally, the water population is measured exclusive of other water populations in the sample.

The features of a T2 relaxation curve, including the range of T2 values associated with a particular signal, may vary based on the instrument (e.g., a T2reader or a Bruker minispec) used to collect data. Likewise, the range of T2 values for a given sample may depend on the material used to construct the tubes (e.g., plastic or glass) containing the sample during T2 measurements. The invention encompasses the use of any magnetic resonance instrument and any sample container in the collection of a 3D data set used in the analysis of a sample.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

This application claims benefit of U.S. Provisional Application No. 61/537,396, filed Sep. 21, 2011, and U.S. Provisional Application No. 61/576,607, filed Dec. 16, 2011, each of which are hereby incorporated by reference.

The invention claimed is:

1. A method of measuring LAL gelation in a sample comprising an endotoxin, the method comprising the steps of:
   (a) mixing said sample with LAL reagent to form a mixture in which the endotoxin produces coagulin, thereby resulting in LAL gelation;
   (b) at a predetermined time following the mixing of step (a), measuring the NMR relaxation rate of water in the mixture, wherein the NMR relaxation rate is selected from the group consisting of T1, T2, T1/T2 hybrid, $T_{1rho}$, $T_{2rho}$, and $T_2^*$ and corresponds to a level of LAL gelation in the mixture; and
   (c) on the basis of said level of LAL gelation, determining a level of the endotoxin in said sample, wherein said method is capable of detecting 0.0001 EU/mL in said mixture.

2. The method of claim 1, wherein step (b) is repeated and a change in said NMR relaxation rate is observed at two or more time points following step (a).

3. The method of claim 2, further comprising calculating said change in said NMR relaxation rate, and, on the basis of said change, determining the endotoxin level in said sample.

4. The method of claim 1, wherein step (c) further comprises comparing the NMR relaxation rate to a predetermined threshold value.

5. The method of claim 1, wherein said endotoxin level is determined within 20 minutes of performing the mixing of step (a).

6. The method of claim 1, wherein said mixture comprises from 10% to 50% of the amount of LAL reagent typically used in a turbidimetric assay.

7. The method of claim 1, wherein said sample comprises a light scattering or light absorbing composition.

8. The method of claim 1, further comprising determining from the NMR relaxation rate a magnetic resonance parameter value or set of values correlated to at least one population of water in said sample.

9. The method of claim 8, comprising monitoring protons in water.

10. The method of claim 8, comprising monitoring oxygen atoms in water.

11. The method of claim 1, wherein said NMR relaxation rate measurements comprises a T2 measurement.

12. The method of claim 8, wherein said magnetic resonance parameter value or set of values comprise a T2 parameter value.

13. The method of claim 8, wherein said magnetic resonance parameter value or set of values comprise an amplitude parameter value.

* * * * *